(12) United States Patent
Lorincz

(10) Patent No.: US 6,567,214 B2
(45) Date of Patent: May 20, 2003

(54) MICROSCOPE SLIDE HAVING CULTURE MEDIA AND METHOD FOR USE

(76) Inventor: Andrew E. Lorincz, 3628 Belle Meade Way, Mountain Brook, AL (US) 35223-1508

( * ) Notice: Subject to any disclaimer, the term of this patent is extended or adjusted under 35 U.S.C. 154(b) by 0 days.

(21) Appl. No.: 09/925,817

(22) Filed: Aug. 9, 2001

(65) Prior Publication Data

US 2001/0050810 A1 Dec. 13, 2001

Related U.S. Application Data

(60) Continuation of application No. 09/399,717, filed on Sep. 21, 1999, now abandoned, which is a continuation-in-part of application No. 09/123,049, filed on Jul. 27, 1998, now abandoned, which is a division of application No. 08/929,234, filed on Sep. 4, 1997, now Pat. No. 5,812,312.

(51) Int. Cl.[7] .......................... G02B 21/34; G01N 21/00
(52) U.S. Cl. ....................... 359/397; 359/396; 359/398; 422/58; 427/2.11
(58) Field of Search ................................ 359/396–398; 356/244, 246; 422/51, 58–60, 101–104; 435/288.3

(56) References Cited

U.S. PATENT DOCUMENTS

| | | | |
|---|---|---|---|
| 3,532,412 A | 10/1970 | Miller | 156/108 |
| 3,551,023 A | 12/1970 | Brackett | 156/60 |
| 3,556,633 A | * 1/1971 | Mutschmann et al. | 359/398 |
| 3,736,042 A | * 5/1973 | Markovits et al. | 359/398 |
| 3,769,171 A | 10/1973 | Grimes et al. | 435/243 |
| 3,930,928 A | 1/1976 | Tapert | 156/556 |
| 4,171,866 A | 10/1979 | Tolles | 356/39 |
| 4,188,246 A | 2/1980 | Lipshaw | 156/57 |
| 4,190,314 A | * 2/1980 | Goldsmith | 359/396 |
| 4,302,480 A | * 11/1981 | Fischer et al. | 427/2 |
| 4,500,509 A | * 2/1985 | Kass | 424/3 |
| 4,545,831 A | 10/1985 | Ornstein | 156/57 |
| 4,635,790 A | 1/1987 | Jackson et al. | 206/210 |
| 4,728,607 A | 3/1988 | Dorn et al. | 435/34 |
| 4,935,374 A | 6/1990 | Jacobs et al. | 436/103 |
| 5,202,230 A | 4/1993 | Kamentsky | 435/6 |
| 5,364,790 A | 11/1994 | Atwood et al. | 435/287.2 |
| 5,561,556 A | * 10/1996 | Weissman | 359/396 |
| 5,569,607 A | * 10/1996 | Simon et al. | 436/46 |
| 5,661,029 A | * 8/1997 | Self et al. | 435/288.3 |
| 5,681,712 A | * 10/1997 | Nelson | 359/398 |
| 6,052,224 A | 4/2000 | Richardson | 359/398 |

FOREIGN PATENT DOCUMENTS

GB 2163866 3/1986

OTHER PUBLICATIONS

Petcharuttana et al., Fluorescence microscopy of DES–induced morphologic transformation in unfixed, cultured cells.*J. Oral Pathol Med,* 18: 451–456 (1989).

Lorincz et al, Supravital Microscope Fluorescence Technique Used to Identify Spirochetes, *Annals of Clinical and Laboratory Science,* 19: 313–314 (1989).

Lorincz, Andrew E., One Step On–Site Epi–Fluorescence Detection of Fungi: A Possible Alternative to KOH Screening. *Annals of Clinical and Laboratory Science,* 23: 308 (1993).

Lorincz, Andrew E., Rapid Method for the Indentification of Mycoplasma Organisms. *Manual of Procedures for the Application of Nucleic Acid Probes and Monoclonal Antibodies and Human Disease,* pp. 163–165 (1987).

Hiraoka et al., Diagnosis of urinary tract infection by urine microscopy using a disposable counting chamber. *Scand J Clin Lab Invest,* 53: 705–709 (1993).

* cited by examiner

*Primary Examiner*—Thong Nguyen
(74) *Attorney, Agent, or Firm*—Kenneth M. Bush; Bush IP Law Group

(57) ABSTRACT

A microscope slide having a well formed therein, wherein the well is filled with culture media. The slide is designed for on-site collection, staining, and viewing of cells in biological fluid and tissue samples, preferably with an epifluorescence microscope. This novel slide permits point-of-care screening in a matter of minutes of any biological fluid or tissue sample for presence of infectious agents, after which, the slide can be transported to a central lab for culture and/or definitive identification.

17 Claims, 3 Drawing Sheets

MICROSCOPE SLIDE HAVING CULTURE MEDIA AND METHOD FOR USE

RELATED PATENTS

This application is a continuation of U.S. patent application Ser. No. 09/399,717, filed on Sep. 21, 1999, now abandoned, which is a continuation-in-part of U.S. patent application Ser. No. 09/123,049, filed on Jul. 27, 1998, now abandoned, which in turn is a divisional application of U.S. patent application Ser. No. 08/929,234, filed on Sep. 4, 1997, now U.S. Pat. No. 5,812,312.

FIELD OF THE INVENTION

The present invention relates to microscope slides. More particularly, the present invention relates to an improved microscope slide having a well formed therein, wherein the well is filled with culture media. More particularly, the present invention relates to an improved microscope slide designed for on-site collection, staining, and viewing of cells in biological fluid and tissue samples, after which, the slide can be transported to a central lab for culture and/or definitive identification.

BACKGROUND OF THE INVENTION

Presently used methods for analyzing biological specimens for cellular dysmorphology and microbial infection are both time consuming and costly. For example, tissue samples taken from patients, such as needle biopsies and aspirates, typically must be chemically fixed and stained, and oftentimes sectioned, and then prepared on microscope slides before they can be examined. Additionally, in many circumstances, biological samples must first be cultured before the processing steps mentioned above. Another problem concerns the resulting specimen itself, which is usually substantially altered by fixation and fragmentation during the preparation process.

Another problem concerns unnecessary procedures, which again waste time and resources. In a typical urinalysis, for example, a sample is obtained from a patient and subjected to a "dipstick" screening procedure. Light microscopic examination of the sediment following centrifugation of the urine specimen is then performed. If there are any abnormal results from these examinations, the sample is transferred to a laboratory for microbiological culture and antibiotic sensitivity studies, which typically take from 24 to 48 hours, or longer, to obtain the results. However, in many instances as much as 80% of the urine samples submitted for culture and sensitivity studies do not result in the detection of clinically significant bacterial presence, thus wasting valuable technician time and laboratory material resources. Furthermore, in rural areas or third world countries, samples must typically be transported to remote locations for evaluation, which can magnify the problem due to additional time delays, plus additional transportation and handling costs.

The present invention represents a departure from standard microbial and morphologic studies in the practice of clinical medicine by modifying microscope slides to be used as screening tools for on-site determination of possible infection or presence of cellular dysmorphology. The slides of the present invention avoid the time associated with preparing traditional slide preparations and they further provide a simpler and less expensive alternative to the currently utilized microscopy screening procedures, such as the Gram histochemical stain used to detect bacteria and other microorganisms; the potassium hydroxide (KOH) preparation used to screen for fungi and yeast; and the darkfield examination used to detect spirochetes and other microorganisms less than 1 micrometer (uM) in diameter or size, such as mycoplasma, other mollicutes, legionella, etc.

SUMMARY OF THE PRESENT INVENTION

It is an object of the present invention to provide a microscope slide adapted for supravital staining of cells in a biological fluid or tissue sample.

It is another object of the present invention to provide a microscope slide that allows for immediate on-site screening of a biological fluid or tissue sample.

It is another object of the present invention to provide a microscope slide having a well filled with culture media.

These and other objects of the present invention are accomplished through the use of a microscope slide having a well formed therein, wherein the well is filled with culture media. The slide is designed for on-site collection, staining, and viewing of cells in biological fluid and tissue samples, preferably with an epi-fluorescence microscope, after which, the slide can be transported to a central lab for culture and/or definitive identification. This novel slide permits point-of-care screening in a matter of minutes of any biological fluid or tissue sample (e.g. urine, blood, sputum, spinal fluid, amniotic fluid, tears, needle aspirates, semen, tissue touch preparations, plant sap, etc.) for presence of infectious agents (e.g. bacteria, including mycoplasma-sized mollicutes, spirochetes, fungi, parasites, etc.).

These and other objects and advantages of the invention will become apparent from the following detailed description of the preferred embodiment of the invention.

BRIEF DESCRIPTION OF THE DRAWINGS

A microscope slide embodying features of the invention is described in the accompanying drawings which form a portion of this disclosure and wherein.

DETAILED DESCRIPTION OF THE PREFERRED EMBODIMENT

The present application is a continuation of U.S. patent application Ser. No. 09/399,717, which is a continuation-impart of U.S. patent application Ser. No. 09/123,049, both of which are incorporated herein by reference. The present invention is a self-staining microscope slide designed for supravital staining of cells and microorganisms in a biological fluid or tissue sample, and adapted for immediate visual or instrumental examination of the stained cells. The American Heritage Dictionary of the English Language (3rd ed., 1992) defines "supravital" as relating to or capable of staining living cells after their removal from a living or recently dead organism. Thus, the present invention allows immediate, on-site staining of unfixed cells from a biological sample which can be immediately viewed for preliminary diagnosis of a plurality of conditions. Since supravital staining is incorporated in the prepared slides, the time and cost of drying, chemical fixation, and/or sectioning of specimens may be completely avoided.

A more complete understanding of the present invention may be obtained by reference to the accompanying drawings, wherein a microscope slide 11 according to the present invention comprises a viewing area 12 having a well 13 formed therein, wherein the well is filled with solidified culture media 14, such as agar media. Carefully selected culture media provides optimal conditions for growth of various pathogens. Thus, after a sample has been initially screened, the slide can be transported to a central lab for culture and/or definitive identification. Some examples of agar media include blood supplemented agar, which can display hemolytic action, and Sabouraud's dextrose agar for fungal culture. Antibiotics and/or other chemical agents can be added to blood agar to create a selective medium, such as colistin-nalidixic acid (CAN) agar or phemylethyl alcohol (PEA) agar, which are used to inhibit the growth of gram-negative bacilli while permitting growth of gram-positive bacteria. Gram-negative bacilli can be separated from gram-positive bacteria by using a bile salt and dye in a medium such as MacConkey's agar, which identifies lactose-positive from lactose-negative bacterial colonies, thus making it a selective and differential medium. A reference teaching various solidified culture media appropriate for use in the present invention is *Clinical Diagnoses and Management by Laboratory Methods, 19$^{th}$ Edition*, by John B. Henry, M. D. (W. B. Saunders Co., 1996), incorporated herein by reference.

Figure 1:
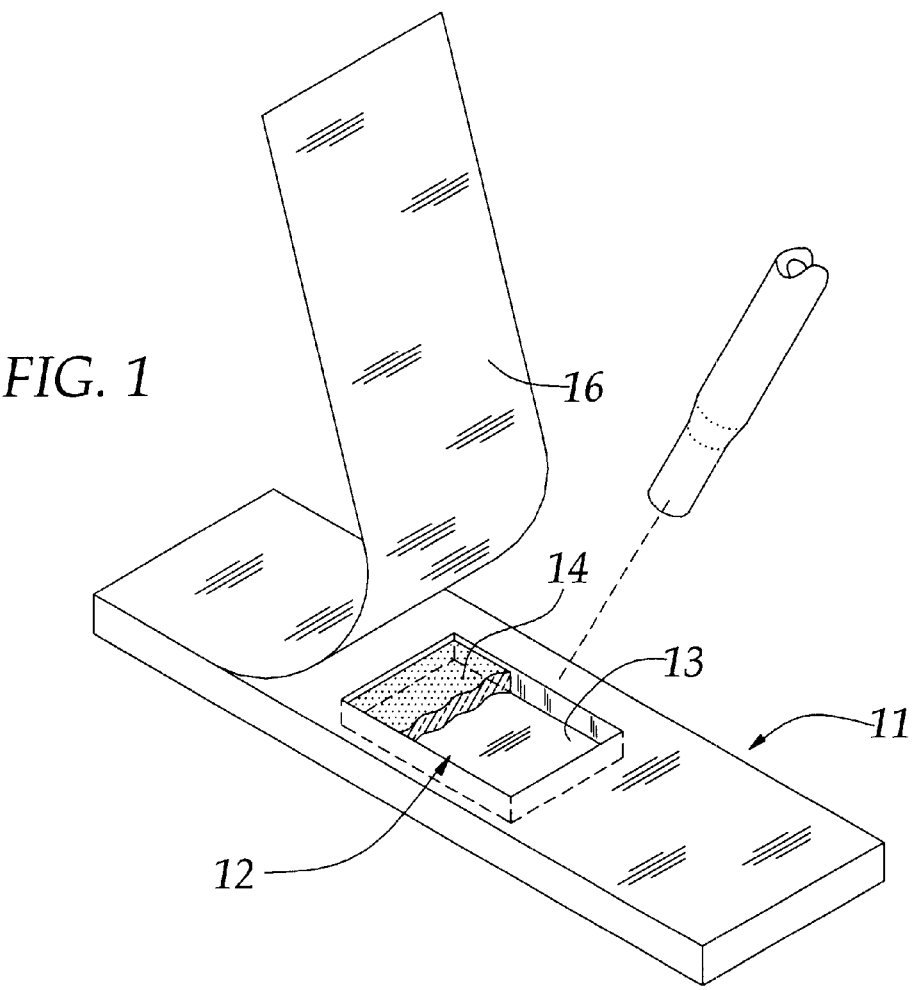
FIG. 1 is a perspective view of the present invention having a flexible film cover slip peeled back so that a sample can be placed on the viewing area of the slide.
Figure 2:
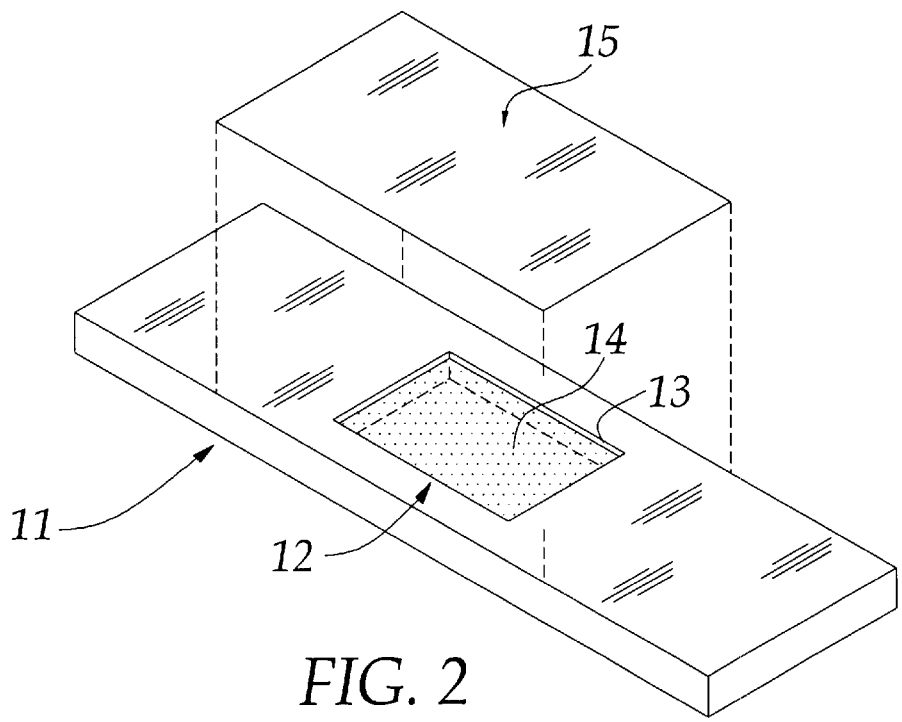
FIG. 2 is an exploded perspective view of the present invention having a rigid cover slip.
Figure 3:
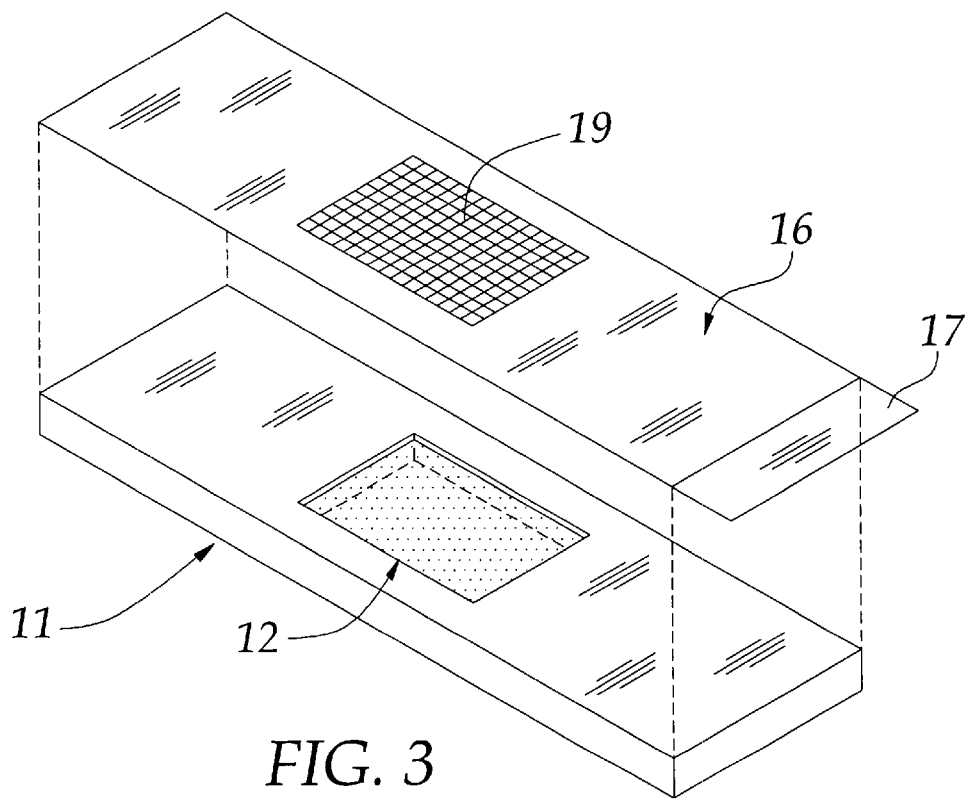
FIG. 3 is an exploded perspective view of the present invention having a flexible film cover slip.
Figure 4:
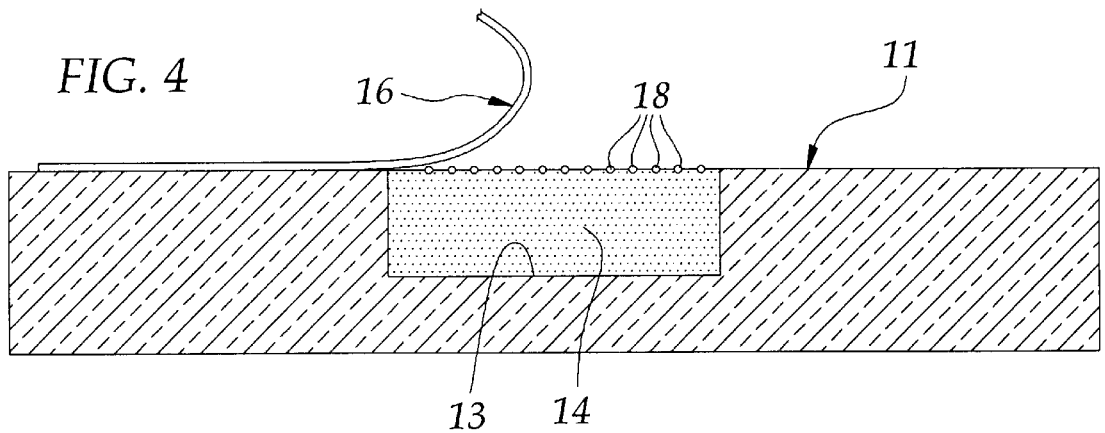
FIG. 4 is a sectional view of the present invention.

A supravital dye for staining the sample is preferably incorporated into the culture media 14 or placed on an exposed surface thereof, or the dye can be applied to the underside of transparent covering means, such as a rigid cover slip 15 or flexible film 16. Preferably, a flexible film 16, shown in FIGS. 1 and 3, is attached to the slide 11 with a weak adhesive such that the film can be peeled back to expose the viewing area 12 for application of the sample and replaced such that the sample intermixes with the dye, thereby staining any cells in the sample for immediate viewing under a microscope. The exposed surface of the solidified culture media 14 can be flush with the slide surface, as shown in FIG. 4, or it can be slightly recessed, as shown in FIGS. 1–3, to accommodate more voluminous samples. In either case, the covering means should be flush with the sample to permit proper viewing under a microscope.

The supravital dyes are preferably water soluble fluorochromes, such as acridine orange, acridine yellow, etc., in appropriately buffered concentrations. A fluorescence or epi-fluorescence microscope is required to view the fluorescent stained samples, and preferably the latter because the media effects fluorescent light dispersion therethrough. By staining the sample with a fluorochrome and utilizing an epi-fluorescent microscope for viewing, the visualization of the structures in the sample is greatly enhanced compared to visualization with phase contrast or similar light microscopy. This is analogous to viewing the moon at night compared to viewing the moon during the day. The vital dye will diffuse into a living cell or microorganism, without killing the cell, and complex with macromolecules such as DNA, glycosaminoglycans, lipopolysaccharides, etc., which are present in the cell. The dye-macromolecule complexes are rendered fluorescent and can be visualized after excitation with appropriate light frequencies from mercury lamps, halogen lamps, tungsten lamps, etc.

The microscope slide 11 preferably comprises a plastic material because it is lightweight, facilitating transport and storage, and not prone to breakage as glass slides. The slide 11 can be transparent, opaque, or tinted. The slides can be easily sterilized (e.g. via autoclave or microwave oven) for disposal, or alternatively, the slides can be recycled to reduce biological wastes. The film 16 comprises a flexible transparent material having an adhesive on one side, such as Scotch™ brand tapes (3M Company), for placement over the viewing surface of the slide 11 such that the adhesive surface is in contact with the viewing surface of the slide. In an alternate embodiment, the adhesive can be placed only along the margins of the film so that no adhesive overlaps the viewing area 12. The film 16 preferably has a portion 17 on at least one end having no adhesive thereon such that the portion 17 acts as a grip for handling the film 16.

Other features which are beneficial include the addition of size references, such as fluorescent microspheres of known dimension (e.g. 1 uM), to the surface of the slide or the film such that they coincide with the field of focus of the specimen. For example, microspheres 18 can be incorporated within the dye or they can be applied to the exposed surface of the culture media 14, as illustrated in FIG. 4. This facilitates focusing the microscope and provides an internal reference standard for size, which is preserved for photomicrography or video image capture. Other reference standards, such as a sizing grid 19 shown in FIG. 3, can also be incorporated as by etching or photographic reproduction onto the surface of the film to allow sizing and quantitation of cells, microorganisms or the like.

Since the collected biological fluid sample (e.g. blood, urine, sputum, bronchial or gastric washings, spinal fluid, synovial fluid, cervical smear, semen, prostate secretion, tears, needle biopsy specimens, amniotic fluid, plant sap, etc.) is not dried or chemically fixed, the morphology and mobility of the intact cells and/or microorganisms is maintained. Nuclear morphology of the living cells is preserved for immediate visual (or image) analysis facilitating determination of the presence or absence of malignant dysmorphology. Similarly, the presence of abnormal macromolecular "storage" in cell (e.g. in amniotic fluid, white blood cells, cultured fibroblasts) can be readily observed. Although all DNA containing cells are non-specifically stained by the fluorochrome, the size, shape and movement patterns of any microorganisms present may be helpful in serving for preliminary identification of the microorganisms. Additionally, the presence or absence of viral inclusion bodies can also be observed, which is of some consequence in examining oral and nasal smears.

Nowadays, with the availability of portable fluorescence microscopes that can even be powered by an automobile battery, the ability to use the slides can be readily adapted for field use in developing countries, rural clinics, mobile vans, etc. If visual screening confirms the presence of bacterial or fungal infection, or protozoan infestation, the same specially prepared slides that are used for on-site screening, can be used for specimen transfer. Such transfer to a peripheral or reference laboratory permits further culture as well as definitive identification via histochemical study or DNA analysis (e.g. PCR, ELISA, monoclonal antibody studies). The slides preserve the microorganism intact and if the appropriate culture medium suited for optimal growth is incorporated into the slide, the need to take a second sample for culture is precluded and the need for subculturing by the reference lab may also be avoided. Furthermore, photomicrographs or digital imaging techniques can permanently capture what can be visualized in the epi-fluorescence microscope. Transmission of these digital images to remote central laboratories for evaluation is also a possibility.

By utilizing the slides in the operating room, examination of biopsy tissue touch preparations or needle biopsies might obviate the need for the expensive microtomes and cytotechnicians now required for present quick-frozen tissue section studies. Turnaround times for results would also be considerably faster. The delays between specimen collection and reporting of laboratory results do not exist when testing is conducted on-site, which permits immediate action by the physician once testing is completed. Thus, this methodology should significantly improve clinical practice guidelines for physicians ordering laboratory tests. For example, an uncentrifuged, supravitally stained urine sample on the present slide can be immediately visualized with an epifluorescent microscope, allowing superior visualization of the structures in the sample to substantially increase the accuracy of diagnosing urinary tract infections. The principle and methodology are scientifically accurate, reproducible, easily taught and easily learned; even by nonprofessional laboratory technicians. The slides can also be used to examine plant specimens, such as plant sap, for microbial infections and the like.

The slides of the present invention provide a simpler and less expensive alternative to the currently utilized microscopy screening procedures, such as the Gram histochemical stain used to detect bacteria and other microorganisms; the potassium hydroxide (KOH) preparation used to screen for fungi and yeast; and the darkfield examination used to detect spirochetes. Additionally, the slides permit detection of mycoplasma species and other mollicutes (smallest known bacteria that do not have cell walls), which cannot be visualized by standard light transmission microscopes.

Production costs should be less expensive than the costs of producing glass microscope slides and glass cover slips. Chances for breakage and infecting clinical personnel should be diminished. The quantity of cultural media required is considerably less than now used in traditional petri-dish culture plates or slant tube culture equipment. The weight of the slides is far less than that of glass slides or culture plates, thus facilitating transport and storage. Importantly, laboratory wastes is concomitantly reduced.

It is to be understood that the form of the invention shown is a preferred embodiment thereof and that various changes and modifications may be made therein without departing from the spirit of the invention or scope as defined in the following claims.

Having set forth the nature of the invention, what is claimed is:

1. A microscope slide for supravitally staining a biological sample for immediate viewing with a microscope, comprising:
    a) an elongated member having a well formed therein, wherein said well is filled with solidified culture media;
    b) a supravital dye for staining the sample; and
    c) means for covering said well such that said dye is in contact with a surface of said culture media between said elongated member and said covering means, wherein said covering means can be removed to expose said surface of said culture media for placing the sample thereon and replaced such that the sample can be viewed under the microscope, wherein said covering means has a lower surface which abuts the sample when said covering means is replaced over said culture media.

2. A microscope slide according to claim 1, wherein said dye is attached to said lower surface of said covering means.

3. A microscope slide according to claim 1, wherein said dye is applied to said exposed surface of said culture media.

4. A microscope slide according to claim 1, wherein said dye is intermixed with said culture media such that a portion of said dye is exposed at said exposed surface of said culture media.

5. A microscope slide according to claim 1, further comprising reference markers to assist in focusing a microscope, wherein said reference markers are located along an exposed surface of said culture media.

6. A microscope slide according to claim 1, further comprising a reference standard for measuring the size and quantity of cells or microorganisms in the sample, wherein said reference standard comprises a grid printed on said covering means.

7. A method for evaluating biological fluids for the presence of microorganisms, comprising the steps of:
    a) collecting a biological fluid sample;
    b) applying the sample to an exposed surface of solidified culture media, wherein said culture media is in a well of a microscope slide;
    c) covering the well with a cover, wherein said cover has a lower surface which abuts the sample when said cover is placed over said well such that the sample is dispersed between said exposed surface of said culture media and said lower surface of said cover;
    d) adding a supravital dye to the sample, wherein said dye is attached to at least one of said surfaces such that said dye will diffuse into the sample and stain any microorganisms therein;
    e) viewing the stained sample to determine whether any microorganisms are present in the sample; and
    f) transporting the microscope slide containing the stained sample to a remote location for culture and identification of any microorganisms present in the sample.

8. A method according to claim 7, wherein the stained sample is viewed through an epi-fluorescence microscope.

9. A method according to claim 7, wherein said dye is attached to said lower surface of said cover.

10. A method according to claim 7, wherein said dye is applied to said exposed surface of said culture media.

11. A method according to claim 7, wherein said dye is intermixed with said culture media such that a portion of said dye is exposed at said exposed surface of said culture media.

12. A method according to claim 7, wherein said culture media has reference markers along an exposed surface thereof to assist in focusing a microscope.

13. A method according to claim 7, wherein said cover has a grid printed thereon for measuring the size and quantity of cells or microorganisms in the sample.

14. A method for evaluating biological fluids for the presence of microorganisms or cellular dysmorphology, comprising the steps of:
    a) collecting a biological fluid sample;
    b) applying the sample to an exposed surface of solidified culture media, wherein said culture media is in a well of a microscope slide;
    c) covering the well with a cover, wherein said cover has a lower surface which abuts the sample when said cover is placed over said well such that the sample is dispersed between said exposed surface of said culture media and said lower surface of said cover;

d) adding a supravital dye to the sample, wherein said dye is attached to at least one of said surfaces such that said dye will diffuse into the sample and stain any microorganisms or cells therein; and e) viewing the stained sample to determine whether microorganisms or cellular dysmorphology are present in the sample.

15. A method according to claim 15, wherein the stained sample is viewed through an epi-fluorescence microscope.

16. A method according to claim 15, further comprising the step of (f) transmitting images of the stained sample to a remote location for evaluation.

17. A method according to claim 15, further comprising the step of (f) transporting the microscope slide containing the stained sample to a remote location for culture and identification of any microorganisms present in the sample.

* * * * *